United States Patent [19]
Christy

[11] 3,992,547
[45] Nov. 16, 1976

[54] 4-(5H-DIBENZO[a,d]CYCLOHEPTEN-5-YLIDENE)-1-METHYLPIPERIDINE-N-OXIDE ISOMER

[75] Inventor: Marcia E. Christy, Perkasie, Pa.

[73] Assignee: Merck & Co., Inc., Rahway, N.J.

[22] Filed: Nov. 20, 1974

[21] Appl. No.: 525,324

[52] U.S. Cl. .......................... 424/267; 260/293.62
[51] Int. Cl.² .................................. C07D 211/70
[58] Field of Search ............... 260/293.62; 424/267

[56] References Cited
UNITED STATES PATENTS

| | | | |
|---|---|---|---|
| 3,014,911 | 12/1961 | Engelhardt | 260/293.62 |
| 3,642,808 | 2/1972 | Schroter et al. | 260/293.62 |
| 3,851,059 | 11/1974 | Prugh | 424/267 |

OTHER PUBLICATIONS

Ebnother et al., Helv. Chim. Acta 1965, vol. 48, pp. 1237–1249.
Winthrop et al., J. Org. Chem. 1962, vol. 27, pp. 230–240.
Ishwariah Chem. Abst. 1970, vol. 72, No. 39328z.
Mertz et al., Chem. Abst. 1970, vol. 72, No. 20541s.
Nakayama et al., Chem. Abst. 1973, vol. 78, 97494k.
Vignoli et al., Chem. Abst. 1966, vol. 65, Col. 16793.

*Primary Examiner*—Natalie Trousof
*Attorney, Agent, or Firm*—Harry E. Westlake, Jr.; James A. Arno; William H. Nicholson

[57] ABSTRACT

A specified geometrical isomer of 4-(5H-dibenzo[a,d]cyclohepten-5-ylidene)-1-methylpiperidine-N-oxide is disclosed to have pharmaceutical utility as an appetite stimulant. Also disclosed are processes for the preparation of such compound; pharmaceutical compositions comprising such compound; and methods of treatment comprising administering such compound and compositions.

3 Claims, No Drawings

4-(5H-DIBENZO[a,d]CYCLOHEPTEN-5-YLIDENE)-1-METHYLPIPERIDINE-N-OXIDE ISOMER

BACKGROUND OF THE INVENTION

This invention relates to a specified geometrical isomer of 4-(5H-dibenzo[a,d]cyclohepten-5-ylidene)-1-methylpiperidine-N-oxide (hereinafter referred to as β-cyproheptadine N-oxide) as an appetite stimulant; also contemplated within the scope of the present invention are pharmaceutically acceptable acid addition salts thereof. Further, this invention relates to processes for the preparation of such compounds; to pharmaceutical compositions comprising such compounds; and to methods of treatment comprising administering such compounds and compositions when an appetite stimulant is indicated. The free base form of the β-cyproheptadine N-oxide of the present invention has the following structural formula I:

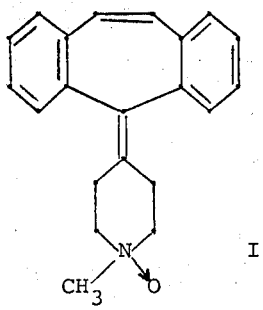

Unexpectedly it has been discovered that isomeric resolution of 4-(5H-dibenzo[a,d]cyclohepten-5-ylidene)-1-methylpiperidine-N-oxide provides a geometrical isomer (β-cyproheptadine N-oxide, characterized below) which is an appetite stimulant substantially devoid of unwanted side effects such as the antiserotonin activity of the unresolved, naturally occuring isomeric mixture. (α and β forms). Said isomeric mixture is generically disclosed in U.S. Pat. No. 3,014,911 Dec. 26, 1961) to have antiserotonin and antihistamine activity.

Accordingly, it is an object of the present invention to provide β-cyproheptadine N-oxide and its pharmaceutically acceptable salts as appetite stimulants in a form substantially free (less than 15 wt. % contamination) of its corresponding α-geometrical isomer (hereinafter characterized). It is a further object of this invention to provide processes for the preparation of such compounds; pharmaceutical compositions comprising such compounds; and methods of treatment comprising administering such compounds and compositions when an appetite stimulating effect is indicated.

DETAILED DESCRIPTION OF THE INVENTION

The 4-(5H-dibenzo[a,d]cyclohepten-5-ylidene)-1-methylpiperidine-N-oxide may conveniently be prepared by oxidation of cyproheptadine with oxidizing agents such as hydrogen peroxide or peracids such as m-chloro-perbenzoic acid and the like according to the procedure of U.S. Pat. No. 3,014,911, incorporated herein by reference.

Resolution of the geometrical isomers, α & β, may be done by chromatographic methods such as column chromatography packed with silica gel, cellulose or the like. With the physical characterizing data (nmr spectra, melting point, chromatographic $R_f$ value on silica gel, and pharmacological characterization) of the respective isomers (below) as means of identification, alternate means of isomeric resolution are readily evaluated.

Suitable pharmaceutical salt forms of the β-cyproheptadine N-oxide of the present invention may be prepared by conventional means. Salt forms are the most preferred and include: the hydrochloride, sulfate, phosphate, citrate, tartrate, succinate and the like. These salts are generally equivalent in potency to the free base form taking into consideration the stoichiometric quantities employed.

In the method of treatment and pharmaceutical composition aspects of the present invention it is noted that the precise unit dosage form and dosage level depend upon the case history of the individual being treated and consequently are left to the discretion of the therapist. In general, however, the compounds of the present invention produce the desired effect of appetite stimulation when given at from about 0.01 to about 10.0 mg. per kg. body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspensions comprising from about 0.01 to about 10.0 mg. of the compounds of this invention per kg. body weight given daily. Thus, for example, tablets given 2–4 times per day comprising from about 0.5 to about 50 mg. of the compounds of this invention are suitable for human treatment. Sterile solutions (representatively given for human treatment) for injection comprising from about 0.1 to about 10.0 mg. of the compounds of this invention given two to four times daily are also suitable means of delivery.

The following examples representatively illustrate but do not limit the product, compositional or method of treatment aspect of the present invention.

EXAMPLE 1

Cyproheptadine N-Oxide
(4-(5H-Dibenzo[a,d]cyclohepten-5-ylidene)-1-methylpiperidine-N-oxide)

To a stirred and ice-cold solution of 14.8 g. (0.0515 mole) of cyproheptadine in 150 ml. of absolute $CH_3OH$, 30% hydrogen peroxide, (18 g.,) is added in portions. Stirring is continued at 25° C. until the precipitated solid dissolves and the solution is held at room temperature for 10 days. The resulting solution is stirred with a suspension of 200 mg. of 5% Pt/C (platinum black) in 1 ml. of $H_2O$ until the excess peroxide is destroyed. Evaporation of the filtered solution under reduced pressure at 35° C. provides a sticky solid residue which is dried overnight in a vacuum over $P_2O_5$ to yield 15 g. of cyproheptadine N-oxide.

α-Isomer, α-Cyproheptadine-N-oxide

A 10 g. sample of the product cyproheptadine N-oxide is chromatographed on 700 g. of silica gel, eluting with 15% $CH_3OH/CHCl_3$. Fractions containing a single component of $R_f$ 0.5 on a fluorescent silica thin layer plate developed with 20% $CH_3OH/CHCl_3$ were combined. Evaporation of the solvent under reduced pressure left 7.1 g. of solvated white crystalline α-isomer, m.p. 119°–129° C. (dec.). Recrystallization from $H_2O$ gave 5.2 g., m.p. 188°–191° C. after drying 2 days at room temperature at 0.2 mm. Hg. Nuclear magnetic resonance data of the α-isomer in $CDCl_3$ against tetramethyl silane internal standard: δ 3.07 (S,3,N-$CH_3$), δ 4.00 (S,1,$H_2O$), δ 6.97 (S,2,H-10 and H-11), 7.3 (m,8,aromatic protons).

Analysis Calc. for: $C_{21}H_{21}NO.1/2H_2O$: Calc.: C, 80.71; H, 7.10; N, 4.48. Found: C, 80.73; H, 7.15; N, 4.42.

The α-hydrochloride is prepared by precipitating fron a saturated solution of the base in ethanol on addition of 6M HCl. Recrystallization from absolute ethanol provide α-cyproheptadine N-oxide hydrochloride hemihydrate, $C_{21}H_{21}NO.HCl.1/2H_2O$, m.p. 205°–211° C. (dec.).

Analysis Calc. for: $C_{21}H_{21}NO.HCl.1/2H_2O$: Calc.: C, 72.30; H, 6.64; N, 4.02. Found: C, 72.39; H, 6.76; N, 4.03.

β-Isomer, β-Cyproheptadine-N-Oxide

Chromatographic fractions containing a single component of $R_f$ 0.4 on a fluorescent silica thin layer plate developed with 20% $CH_3OH/CHCl_3$ were combined. Evaporation of the solvent under reduced pressure left 2.4 g. of white crystalline β-isomer, m.p. 194°–199° C. (dec.). Nuclear magnetic resonance data of the β-isomer in $CDCl_3$ against tetra methyl silane internal standard: δ 3.28 (S,3,N-$CH_3$), δ 6.93 (S,2,H-10 and H-11), δ 7.3 (m,8,aromatic protons). The resulting base is converted to the hydrochloride salt by the procedure given above for the α-isomer to provide β-cyproheptadine-N-oxide hydrochloride, m.p. 223°–228° C. (dec.) after drying 2 days at room temperature at 0.1 mm. Hg.

Analysis Calcd. for: $C_{21}H_{21}NO.HCl$: Calc.: C, 74,21; H, 6.53; N, 4.12. Found: C, 74,59; H, 6.37; N, 4.17.

Isomeric purity of the above-prepared hydrochloride salts is greater than 95% as shown by nuclear magnetic resonance in $D_2O$ and thin layer chromatography (fluorescent silica, using the following solvent system expressed in volume ratio: 10 benzene : 80 dioxane : 10 conc. $NH_4OH$).

EXAMPLE 2

Pharmaceutical compositions

A typical tablet containing 1 mg. β-cyproheptadine-N-oxide per tablet is prepared by mixing together with the active ingredient calcium phosphate, lactose and starch in the amounts shown in the tables below. After these ingredients are thoroughly mixed, the appropriate amount of magnesium stearate is added and the dry mixture blended for an additional three minutes. This mixture is then compressed into tablets weighing approximately 124 mg. each. Similarly prepared are tablets containing (β-cyproheptadine-N-oxide) hydrochloride.

TABLET FORMULA

| INGREDIENT | MG. PER TABLET |
| --- | --- |
| β-Cyproheptadine-N-oxide | 1 mg. |
| Calcium phosphate | 52 mg. |
| Lactose | 60 mg. |
| Starch | 10 mg. |
| Magnesium stearate | 1 mg. |

TABLET FORMULA

| INGREDIENT | MG. PER TABLET |
| --- | --- |
| (β-Cyproheptadine-N-oxide)-hydrochloride | 1 mg. |
| Calcium phosphate | 52 mg. |
| Lactose | 60 mg. |
| Starch | 10 mg. |
| Magnesium stearate | 1 mg. |

What is claimed is:
1. β-4-(5H-Dibenzo[a,d]cyclohepten-5-ylidene)-1-methylpiperidine-N-oxide substantially free of its corresponding α-geometrical isomer or a nontoxic pharmaceutically acceptable salt thereof.
2. A method of stimulating appetite comprising administering to a patient in need of such treatment a therapeutically effective amount of β-4-(5H-dibenzo[a,d]cyclohepten-5-ylidene)-N-methylpiperidine-N-oxide substantially free of its corresponding α-geometrical isomer or a nontoxic pharmaceutically acceptable salt thereof.
3. A pharmaceutical composition in unitary dosage form for appetite stimulation comprising a therapeutically effective amount of β-4-(5H-dibenzo[a,d]cyclohepten-5-ylidene)-1-methyl-piperidine-N-oxide substantially free of its corresponding α-geometrical isomer or a nontoxic pharmaceutically acceptable salt thereof and a pharmaceutical carrier therefor.

* * * * *